United States Patent
Kinsman et al.

(10) Patent No.: US 6,232,480 B1
(45) Date of Patent: May 15, 2001

(54) METHOD OF MAKING HYDROGENATED ACIDS

(75) Inventors: Donald V. Kinsman, Fort Thomas, KY (US); J. Matthew White, Morrow; David J. Anneken, Cincinnati, both of OH (US)

(73) Assignee: Henkel Corporation, Gulph Mills, PA (US)

( * ) Notice: Subject to any disclaimer, the term of this patent is extended or adjusted under 35 U.S.C. 154(b) by 0 days.

(21) Appl. No.: 09/329,212

(22) Filed: Jun. 10, 1999

Related U.S. Application Data

(63) Continuation-in-part of application No. 08/925,811, filed on Sep. 5, 1997, now abandoned.

(51) Int. Cl.$^7$ ..................................................... C07F 51/36
(52) U.S. Cl. ........................................... 554/147; 554/141
(58) Field of Search ...................................... 554/141, 147

(56) References Cited

U.S. PATENT DOCUMENTS 4,049,520    9/1977    Wagner .

OTHER PUBLICATIONS

Johnson, et al., Fatty Acids In Industry, Marcel Dekker, Inc., Chapter 3, 1989, pp. 73–84.

*Primary Examiner*—Deborah D. Carr
(74) *Attorney, Agent, or Firm*—John E. Drach; Joanne Mary Fobare Rossi

(57) ABSTRACT

A mixture of saturated and unsaturated carboxylic acids are hydrogenated with an effective amount of a hydrogenation catalyst and in the presence of an effective amount of an adsorbent to produce a hydrogenated product having less than about 200 ppm of oxygenated by-products and an iodine value of less than 10.

26 Claims, No Drawings

METHOD OF MAKING HYDROGENATED ACIDS

CROSS-REFERENCE TO RELATED APPLICATIONS

This application is a continuation-in-part of application Ser. No. 08/925,811 filed Sep. 5, 1997, now abandoned, the entire contents of which are incorporated herein by reference.

STATEMENT REGARDING FEDERALLY SPONSORED RESEARCH OR DEVELOPMENT

Not applicable.

BACKGROUND OF THE INVENTION

Mixtures of saturated and unsaturated carboxylic acids are conveniently converted to products substantially free of unsaturation by means of catalytic hydrogenation. Such a process is particularly useful in the commercial production of fatty acids, compounds which are used to make base stocks for soap production, as intermediate raw materials for producing a wide range of surfactants, as foam control agents and precipitants in a variety of cleaning products, as superfatting agents in personal cleansing bars, as softener components, and for a number of other more specialized purposes. Fatty acids are obtained from fats and oils by a process the first step of which is referred to as splitting. Splitting is the hydrolysis of a fat or oil to form three molecules of fatty acid and one molecule of glycerine. The glycerine is separated and refined in a separate operation. The crude split fatty acids are usually then distilled to remove color bodies and odoriferous materials. This sequence of splitting and distilling yields the most basic tallow and coconut fatty acids which are widely used for preparing bar soaps. This basic type of coconut fatty acids also finds use in the preparation of a variety of types of surfactants. While these simple split and distilled tallow and coconut fatty acids do have wide use, many in the soap and detergents industry prefer materials with improved colors, color stabilities and odors. These improvements are often effected by hydrogenation.

In the case of tallow the hydrogenation is a partial hydrogenation. It is generally controlled so as to reduce or totally eliminate the polyunsaturated acids, which are inevitably present in split tallows. Reducing or eliminating the polyunsaturates can significantly improve the color stability of the fatty acids and many soap producers find that this carries through to improving the storage properties of their soap bars. The hydrogenation process also improves the initial color and odor of the partially hydrogenated fatty acids and this also is generally found to carry through to bar soaps. The typical catalyst used for hydrogenation is some type of nickel catalyst and it is a nonselective catalyst. That means that besides reducing polyunsaturated acids to monounsaturated acids—basically oleic acids—it also reduces some amount of unsaturated acid to saturated acid— basically stearic acid. During the hydrogenation step, oxygenated compounds such as alcohols, acids and lactones may be formed which can have a deleterious effect on products and/or processes utilizing such acids. For example, the presence of alcoholic impurities could interfere with the production of acid chlorides. It is therefore desirable to produce a hydrogenated carboxylic acid that does not contain the oxygenated compounds.

BRIEF SUMMARY OF THE INVENTION

Hydrogenated carboxylic acids are made by a process which comprises contacting a mixture of saturated and unsaturated carboxylic acids with a catalyst effective amount of a hydrogenation catalyst and in the presence of an effective amount of an adsorbent to produce a hydrogenated product having less than about 200 ppm of oxygenated by-products and an iodine value of less than about 10. The process may also be carried out by first contacting a mixture of saturated and unsaturated carboxylic acids with a catalyst effective amount of a hydrogenation catalyst to form a hydrogenated product containing oxygenated by-products and then contacting the hydrogenated product with an effective amount of an adsorbent to produce a hydrogenated product having less than about 200 ppm of oxygenated by-products and an iodine value of less than about 10.

BRIEF DESCRIPTION OF THE SEVERAL VIEWS OF THE DRAWING

Not Applicable.

DETAILED DESCRIPTION OF THE INVENTION

The process according to the invention can be applied to the production of any carboxylic acid made by the hydrogenation of a mixture of saturated and unsaturated carboxylic acids. The simplest example is the production of hydrogenated propionic acid having less than about 200 ppm of oxygenated compounds and an iodine value of less than about 10, by the hydrogenation of a mixture of acrylic and propionic acids (propenoic and propanoic acids). The process according to the invention is particularly useful for the commercial production of hydrogenated fatty acids, such as stearic acid, wherein the presence of oxygenated compounds could have a deleterious effect on products and/or processes utilizing such acids. Hydrogenated stearic acid can be made by fully hydrogenating mixtures of saturated and unsaturated tallow fatty acids. Hydrogenation converts these mixtures which contain $C_{18}$ unsaturated acids to stearic acid. During the hydrogenation step, oxygenated compounds such as alcohols, acids and lactones may be formed. The reduction step is typically carried out by contacting the acid mixture with hydrogen in the presence of a catalyst. The typical catalyst used for hydrogenation is some type of nickel catalyst and it is a nonselective catalyst. That means that besides reducing polyunsaturated acids to monounsaturated acids—basically oleic acids—it also reduces some amount of unsaturated acid to saturated acid—basically stearic acid. There is also some conversion of cis-unsaturated acids to transunsaturated acids.

The process according to the invention can be carried out in either of two ways. In one embodiment, a mixture of saturated and unsaturated carboxylic acids is contacted with a catalyst effective amount of a hydrogenation catalyst to produce a hydrogenated product which may contain oxygenated compounds. The hydrogenated product is then contacted with an effective amount of an adsorbent to decrease the amount of any oxygenated compounds to less than about 200 ppm. The process according to the invention results in the degree of the unsaturation of the starting mixture of carboxylic acids being substantially reduced or eliminated. The hydrogenation is carried out until the iodine value is less than about 10, preferably less than about 5 and most preferably less than about 1.

In another embodiment, a mixture of saturated and unsaturated carboxylic acids is contacted with a catalyst effective amount of a hydrogenation catalyst and in the presence of an effective amount of an adsorbent to produce a hydrogenated product having less than about 200 ppm of oxygenated by-products and an iodine value of less than about 10, preferably less than about 5 and most preferably less than about 1. The degree of unsaturation of the starting mixture of carboxylic acids is substantially reduced or eliminated by the process according to the invention. In this embodiment, the adsorbent can be present as part of the catalyst as, for example, the catalyst support or it can be added separately at the beginning of the hydrogenation.

The mixture of saturated and unsaturated carboxylic acids can be composed of any type of saturated and unsaturated carboxylic acids. The carboxylic acids are generally derived from the splitting or hydrolysis of vegetable oil, tallow or grease. Since the process according to the invention is particularly useful for the commercial production of hydrogenated fatty acids, it can be utilized with a fatty acid stream from the processing of any type of fat or oil. For example, the mixture of carboxylic acids can be a crude fatty acid stream resulting from the splitting or hydrolysis of tallow or vegetable oil. The process is particularly suited to carboxylic acids derived from tallow and/or grease such as choice white grease or yellow grease or vegetable oils. Vegetable oils that are particularly preferred are those that contain a high content of saturated or unsaturated C18 fatty acids, examples of which include, but are not limited to, sunflower oil, soybean oil, canola oil, safflower oil, and corn oil. The process can also be used with the carboxylic acids of tall oil and carboxylic acids derived from the splitting or hydrolysis of oils such as rape seed, coconut, linseed, cottonseed, olive or lard. Tallow fatty acids will typically contain somewhere around 50 to 52% unsaturated acids of which all but a few percent, maybe 4% or less, are $C_{18}$ unsaturated acids. Simple split coconut fatty acids contain around 15% of $C_{8-10}$ acids. In one embodiment of the process according to the invention, the mixture of saturated and unsaturated carboxylic acids is solvent separated stearic acid. The mixture of saturated and unsaturated acids may also be obtained from the hydrolysis of sunflower oil, palm oil, tall oil, soybean oil and canola oil. Solvent separated stearic acids are obtained by dissolving tallow fatty acids in a solvent and then passing them through chilled crystallizers where the solid, saturated acids crystallize out to form a slurry which is then filtered. Not all the unsaturated acids are removed by filtration so the crude stearic is subjected to some combination of hydrogenation and distillation combination to produce single, double and triple pressed stearic. What is meant by crude stearic acid is a composition of carboxylic acids derived from a water or solvent separation process comprised of saturated and unsaturated C16 and C18 fatty acids.

In another embodiment of the process according to the invention, the mixture of saturated and unsaturated carboxylic acids is water separated stearic acid. The water separated process is also known as the Henkel process. Water separated stearic adds are obtained by cooling hydrolyzed or split fatty acids, preferably in a scraped surface heat exchanger, to a point where there is slurry of fatty add crystals in the liquid fatty adds. The slurry is mixed with an aqueous solution containing a wetting agent. To this mixture is then added an aqueous solution of an electrolyte. The liquid and fatty acid crystals are separated preferably by centrifugation. The fatty acid crystals are a crude stearic acid mixture. This crude stearic acid mixture can then be used in the process according to the invention. This and other separation processes are described in Fatty Acids in Industry, edited by R. Johnson and E. Fritz, published by Marcel Dekker, Inc., Chapter 3, pages 73–84, 1989.

The catalyst that can be used in the process according to the invention can be any catalyst useful for hydrogenating unsaturated compounds. Such catalysts include but are not limited to platinum, palladium and nickel. The preferred catalyst is nickel. The most preferred catalyst is nickel on acid day, a commercially available example of which is E-428D from Calsicat; Mallinckrodt Inc., Calsicat Div., 1707 Gaskell Ave., Erie, Pa., 16503.

The amount of catalyst that can be used in the process according to the invention is an effective amount which is any amount necessary to bring about the desired degree of hydrogenation. An effective amount will be readily determinable by one of ordinary skill in the art and may depend upon such factors as, for example, the composition of the starting material, the composition of the catalyst, and the hydrogenation temperature. When the process according to the invention is used to make hydrogenated fatty acids, the catalyst amount will typically vary from about 0.7 ppt to about 3.5 ppt (ppt is parts catalyst per thousand parts of carboxylic acid).

The mixture of saturated and unsaturated carboxylic acids can be contacted with a catalyst effective amount of a hydrogenation catalyst at a temperature in the range of from about 180° C. to about 240° C., preferably from about 190° C. to about 230° C., and most preferably from about 200° C. to about 220° C. The pressure at which the hydrogenation is carried out at is from about 200 to about 500 psig, and more preferably from about 300 psig to about 400 psig.

The adsorbent that can be used in the process according to the invention can be carbon black, a commercially available example of which is DARCO® KB from Norit Americas, Inc., 1050 Crown Pointe Parkway, Suite 1500, Atlanta, Ga., 30338; silica, alumina, or clay such as kaolinite, montmorillonite, bentonite, atapulgite, illite and halloysite, a commercially available example of which is FILTROL® Grade 13, Harshaw/Filtrol, 30100 Chagrin Boulevard, Cleveland, Ohio, 44124. When the absorption step follows the hydrogenation step, the absorption step is generally carried out at an elevated temperature. The elevated temperature is used because generally the product of the hydrogenation step, such as stearic acid, has a titer of higher than ambient temperature and would be in a solid or semi-solid state at ambient temperature. The temperature at which the absorption step can be carried out is easily determined by those skilled in the art.

In each embodiment of the present invention as described above, an amount of the adsorbent is used. The effective amount is any amount necessary to decrease the amount of the oxygenated compounds to less than about 200 ppm as determined, for example, by integration of the methylene proton peaks in the 4.9–5.0 δ region of the $H^1$ NMR spectrum.

Any analytical method known to those of ordinary skill in the art useful for the determination of oxygenated by-products as identified herein can be used. The preferred method is by integration of the methylene proton peaks in the 4.9–5.0 δ region of the $H^1$ NMR spectrum as described in Example 2 below. A concentration of 200 ppm is the approximate threshold level for detection of oxygenated by-products in the PFT $H^1$ NMR spectrum.

The following examples are meant to illustrate but not to limit the invention.

EXAMPLE 1

A sample of crude solvent separated stearic acid was hydrogenated to an iodine value of less than 1 with varying amounts of nickel on acid clay catalyst (E-428D) and a clay adsorbent (FILTROL® 13) under the hydrogenation conditions of 205° C., 1 hour and 300 psi hydrogen. The samples were then filtered over dicalite and distilled under a vacuum of 1–3 torr, 1% top cut and a pot temperature of 250° C. and their $H^1$ NMR spectra were taken.

In the control sample (1), the hydrogenation was accomplished using a low catalyst concentration and no added adsorbent. The catalyst and adsorbent were present as one component in that the nickel catalyst was deposited on acid clay which also functioned as the adsorbent. No additional adsorbent was added. Peaks were observed at 4.9–5.0 δ in the $H^1$ NMR spectrum indicating the presence of oxygenated by-products at a level equal to or greater than 200 ppm. In the case of sample (2), the hydrogenation was accomplished using an elevated catalyst level and a corresponding elevated adsorbent level as the catalyst support compared with the control but no separately added adsorbent. No peaks were observed at 4.9–5.0 δ in the $H^1$ NMR spectrum indicating that the level of oxygenated by-products was less than 200 ppm. In the sample (3), the hydrogenation was accomplished using the low catalyst level of the control but in the presence of added adsorbent No peaks were observed at 4.9–5.0 δ in the $H^1$ NMR spectrum indicating that the level of oxygenated by-products was less than 200 ppm. The results as reported in Table 1 below. From Table 1 it is seen that when hydrogenations are carried out in the presence of an effective amount of an adsorbent (samples 2 and 3) which is present either as the catalyst support or added separately, the concentration of the oxygenated by-products is less than 200 ppm.

TABLE 1

| Sample No. | E-428D Catalyst Conc.* | Filtrol ® 13 Conc.* | Conc. 4.9–5.0 δ |
|---|---|---|---|
| 1 | 1.0 ppt | — | 0.02% |
| 2 | 1.7 ppt | — | not detected |
| 3 | 1.0 ppt | 0.7 ppt | not detected |

*ppt is parts per thousand parts of carboxylic acid

EXAMPLE 2

The $H^1$ PFT NMR spectra of the samples in deuterochloroform solvent from Example 1 were obtained using a Varian Unity 400 spectrometer. At least 1000 pulses were collected for each spectra. The spectra were expanded at least 1000 times in order to detect peaks in the 4.9–5.0 δ region. The concentration of the 4.9–5.0 peaks was estimated by comparing it to the —$CH_2CO_2$— peaks between 2.3 and 2.4 δ.

What is claimed is:

1. A process which comprises contacting a mixture of saturated and unsaturated carboxylic acids with an effective amount of a hydrogenation catalyst and in the presence of an effective amount of an adsorbent to produce a hydrogenated product having less than about 200 ppm of oxygenated by-products and an iodine value of less than about 10.

2. The process of claim 1 where the catalyst is nickel on acid clay.

3. The process of claim 1 wherein the amount of the catalyst is from about 0.7 to about 3.5 parts catalyst per thousand parts of carboxylic acid mixture.

4. The process of claim 1 wherein the process is carried out at a temperature of from about 180° C. to about 240° C.

5. The process of claim 1 wherein the adsorbent is carbon black, silica, alumina or clay.

6. The process of claim 1 wherein the mixture of saturated and unsaturated carboxylic acids is comprised of fatty acids.

7. The process of claim 6 wherein the fatty acids are derived from tallow or grease.

8. The process of claim 6 wherein the fatty acids are derived from sunflower oil, palm oil, tall oil, safflower oil, corn oil, rape seed oil, coconut oil, linseed oil, cotton seed oil, olive oil, soybean oil, canola oil and mixtures thereof.

9. A process comprising the steps of:

(1) contacting a mixture of saturated and unsaturated carboxylic acids with an effective amount of a hydrogenation catalyst to produce a reduced product comprised of oxygenated by-products wherein the product has an iodine value of less than about 10;

(2) contacting said hydrogenated acid with an effective amount of an adsorbent to decrease the amount of said oxygenated compounds to less than about 200 ppm.

10. The process of claim 9 where the catalyst is nickel on acid clay.

11. The process of claim 9 wherein the amount of the catalyst is from about 0.7 to about 3.5 parts catalyst per thousand parts of carboxylic acid mixture.

12. The process of claim 9 wherein the process is carried out at a temperature of from about 180° C. to about 240° C.

13. The process of claim 9 wherein the adsorbent is carbon black, silica, alumina or day.

14. The process of claim 9 wherein the mixture of saturated and unsaturated carboxylic acids is comprised of fatty acids.

15. The process of claim 14 wherein the fatty acids are derived from tallow or grease.

16. The process of claim 14 wherein the fatty acids are derived from sunflower oil, palm oil, tall oil, safflower oil, corn oil, tall oil, rape seed oil, coconut oil, linseed oil, cotton seed oil, olive oil, soybean oil, canola oil and mixtures thereof.

17. A process which comprises contacting a mixture of crude stearic acid derived from a solvent separation process or a water separation process with an effective amount of a hydrogenation catalyst and in the presence of an effective amount of an adsorbent to produce a hydrogenated product having less than about 200 ppm of oxygenated by-products and an iodine value of less than about 10.

18. The process of claim 17 where the catalyst is nickel on acid clay.

19. The process of claim 17 wherein the amount of the catalyst is from about 0.7 to about 3.5 parts catalyst per thousand parts of the crude stearic acid mixture.

20. The process of claim 17 wherein the process is carried out at a temperature of from about 180° C. to about 240° C.

21. The process of claim 17 wherein the adsorbent is carbon black, silica, alumina or clay.

22. A process comprising the steps of:

(1) contacting a mixture crude stearic acid derived from a solvent separation process or a water separation process with an effective amount of a hydrogenation catalyst to produce a reduced product comprised of oxygenated by-products wherein the product has an iodine value of less than about 10;

(2) contacting said hydrogenated acid with an effective amount of an adsorbent to decrease the amount of said oxygenated compounds to less than about 200 ppm.

23. The process of claim 22 where the catalyst is nickel on acid clay.

24. The process of claim 22 wherein the amount of the catalyst is from about 0.7 to about 3.5 parts catalyst per thousand parts of carboxylic acid mixture.

25. The process of claim 22 wherein the process is carried out at a temperature of from about 180° C. to about 240° C.

26. The process of claim 22 wherein the adsorbent is carbon black, silica, alumina or clay.

* * * * *